(12) United States Patent
Baker et al.

(10) Patent No.: US 11,759,448 B2
(45) Date of Patent: Sep. 19, 2023

(54) METHODS FOR THE TREATMENT OF INFLAMMATION

(71) Applicants: University of South Florida, Tampa, FL (US); SprainGo, LLC, Tampa, FL (US)

(72) Inventors: Bill J. Baker, Temple Terrace, FL (US); Sofia Kokkaliari, Tampa, FL (US); James Leahy, Lutz, FL (US); Wayne Caleb Williams, Brandon, FL (US)

(73) Assignees: University of South Florida, Tampa, FL (US); SprainGo, LLC, Tampa, FL (US)

( * ) Notice: Subject to any disclaimer, the term of this patent is extended or adjusted under 35 U.S.C. 154(b) by 133 days.

(21) Appl. No.: 17/189,482

(22) Filed: Mar. 2, 2021

(65) Prior Publication Data

US 2021/0267937 A1    Sep. 2, 2021

Related U.S. Application Data

(60) Provisional application No. 62/984,025, filed on Mar. 2, 2020.

(51) Int. Cl.
| | |
|---|---|
| *A61K 31/366* | (2006.01) |
| *A61K 36/15* | (2006.01) |
| *A61K 45/06* | (2006.01) |

(52) U.S. Cl.
CPC .......... *A61K 31/366* (2013.01); *A61K 36/15* (2013.01); *A61K 45/06* (2013.01); *A61K 2236/39* (2013.01); *A61K 2236/51* (2013.01)

(58) Field of Classification Search
CPC .............................. A61K 31/366; A61P 29/00
See application file for complete search history.

(56) References Cited

FOREIGN PATENT DOCUMENTS

| EP | 1925301 | 5/2008 |
| WO | 02/102365 | 12/2002 |

OTHER PUBLICATIONS

Tahara, Akira, and Ken-Ichi Hirao. "Synthesis and conformation of tricyclic 20-norditerpenes with ring-C aromatic." Chemical Communications (London) 7 (1967): 326-328.

Tahara, Akira, and Kenichi Hirao. "Diterpenoids. XIV. Conformational Studies. II. Preferred Conformation of A/B-cis Ring-C Aromatic Tricyclic Diterpenes." Chemical and Pharmaceutical Bulletin 18.10 (1970): 1960-1966.

International Search report and Written Opinion issued for Application No. PCT/US2021/0203 84, dated May 27, 2021.

*Primary Examiner* — Sahar Javanmard
(74) *Attorney, Agent, or Firm* — Meunier Carlin & Curfman LLC (57) ABSTRACT

The present disclosure is directed to methods for the treatment of inflammation or pain, particularly methods using compositions containing a compound of formula (I).

15 Claims, 1 Drawing Sheet

METHODS FOR THE TREATMENT OF INFLAMMATION

CROSS-REFERENCE TO RELATED APPLICATIONS

This application claims the benefit of priority to U.S. Provisional Application No. 62/984,025, filed Mar. 2, 2020, the disclosure of which is incorporated herein by reference in its entirety.

TECHNICAL FIELD

This disclosure relates to methods for the treatment of inflammation, and more particularly to the use of the disclosed compounds in the treatment or prevention of inflammation or disorders or conditions associated therewith.

BACKGROUND

Inflammation is a complex biological process that occurs in response to harmful stimuli, such as for example infections, damage to cells or tissue, or irritants. While inflammation is vital for healing and combating infection, abnormal or excessive inflammation can adversely affect the health, comfort and/or mobility of a subject.

A wide range of anti-inflammatory agents are known, including steroids (such as glucocorticoids) and non-steroidal anti-inflammatory drugs (such as aspirin, ibuprofen, and naproxen). However, these drugs may be ineffective at treating some inflammatory conditions or may be associated with adverse side effects.

For example, some current anti-inflammatory agents have adverse side effects including gastrointestinal damage, renal damage, photosensitivity, hepatic stimulation, headaches, dizziness, Cushing's syndrome, hypertension, hypokalemia, or hypernatremia. Further, some anti-inflammatory agents may not be suitable for certain subjects, such as pregnant subjects or those with inflammatory bowel disease, due to these potential adverse effects.

Thus, there is a clear need for the development of new methods for treating or preventing inflammation, as well as any disorders or conditions associated with inflammation.

SUMMARY

The present disclosure provides methods for the treatment of inflammation and disorders associated therewith, such as pain, by administering a composition containing a compound of formula (I) as described herein.

Thus, in one aspect a method is provided for the treatment or prevention of inflammation in a subject in need thereof comprising administering a composition comprising at least 1 wt. %, based upon the total weight of the composition, of a compound of formula (I) as described herein or a pharmaceutically acceptable derivative thereof.

In another aspect, a method is provided for the treatment of one or more symptoms resulting from inflammation in a subject in need thereof comprising administering a composition comprising at least 1 wt. %, based upon the total weight of the composition, of a compound of formula (I) as described herein or a pharmaceutically acceptable derivative thereof.

In yet another aspect, a method is provided for the treatment of an inflammatory disorder in a subject in need thereof comprising administering a composition comprising at least 1 wt. %, based upon the total weight of the composition, of a compound of formula (I) as described herein or a pharmaceutically acceptable salt or derivative thereof.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Figure 1:
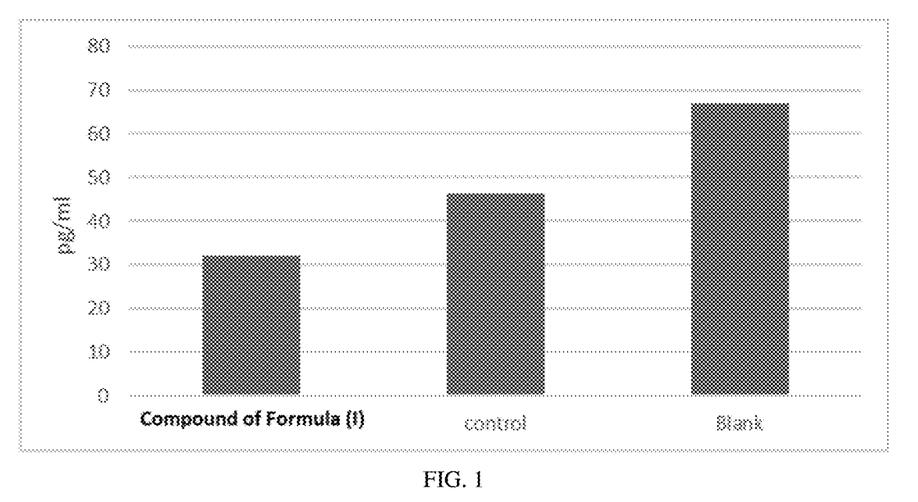
FIG. 1 shows the results of a tumor necrosis factor alpha (TNF-$\alpha$) assay for the compound of formula (I) as described herein. The y-axis shows the levels of TNF-$\alpha$ in picograms per milliliter, with lower values meaning there would be lower inflammation in the cell. These data clearly show that the compound of formula I described herein has inhibitory activity of TNF-$\alpha$.
Figure 2:
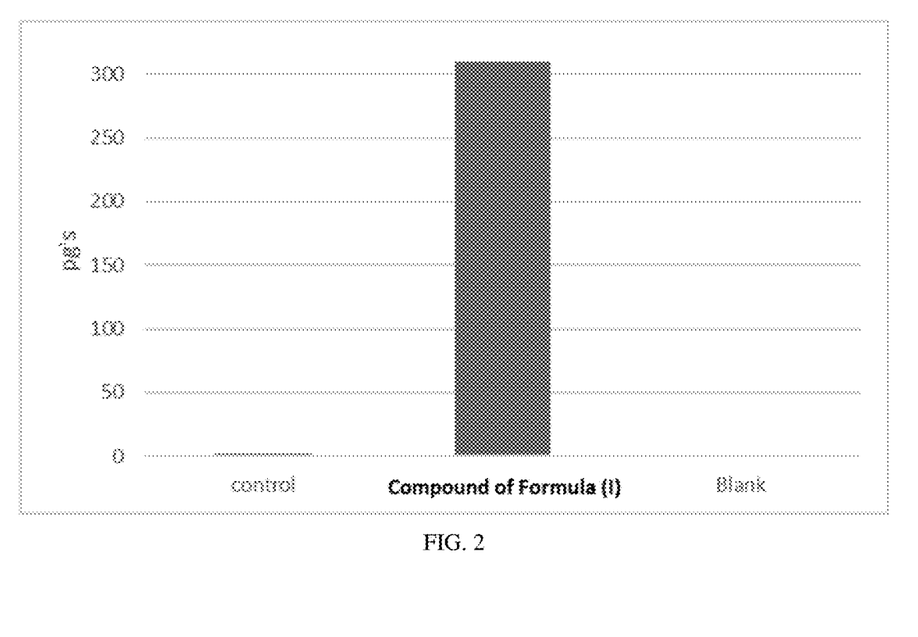
FIG. 2 shows the results of a COX-2 assay for the compound of formula (I) as described herein as compared to a control (diclofenac) and a dimethyl sulfoxide blank. The y-axis shows the level of prostaglandins in the sample. The data show that the compound of formula (I) as described herein has limited to no inhibitory activity on COX-2 as compared to other anti-inflammatories such as the non-steroidal anti-inflammatory drug diclofenac.

The following description of the disclosure is provided as an enable teaching of the disclosure in its best, currently known embodiments. To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are part of the present disclosure. Thus, the following description is provided as illustrative of the principles of the present disclosure and not in limitation thereof.

Definitions

Unless defined otherwise, all technical and scientific terms used herein have the same meaning as commonly understood to one of ordinary skill in the art to which this invention belongs. The following definitions are provided for the full understanding of terms used in the specification.

As used in the specification and claims, the singular form "a", "an", and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount". However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disuifonic, oxalic, isethionic, HOOC—(CH2)n-COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "subject" or "host" can refer to living organisms such as mammals, including, but not limited to humans, livestock, dogs, cats, and other mammals Administration of the therapeutic agents can be carried out at dosages and for periods of time effective for treatment of a subject. In some embodiments, the subject is a human.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, and methods, examples of which are illustrated in the accompanying Examples and Figures.

Methods of Treatment

In one aspect, a method of treating or preventing inflammation in a subject in need thereof is provided comprising administering a composition comprising at least 1 wt. %, based upon the total weight of the composition, of a compound of formula (I):

(I)

or a pharmaceutically acceptable salt or derivative thereof.

In some embodiments, a method for treating inflammation in a subject in need thereof is provided comprising administering a composition comprising at least 1 wt. %, based upon the total weight of the composition, of a compound of formula (I), or a pharmaceutically acceptable salt or derivative thereof.

In some embodiments, a method for diminishing or ameliorating one or more symptoms caused by inflammation in a subject in need thereof is provided comprising administering a composition comprising at least 1 wt. %, based upon the total weight of the composition, of a compound of formula (I), or a pharmaceutically acceptable salt or derivative thereof.

In some embodiments, a method for preventing inflammation in a subject in need thereof is provided comprising administering a composition comprising at least 1 wt. %, based upon the total weight of the composition, of a compound of formula (I), or a pharmaceutically acceptable salt thereof.

In some embodiments, the methods described herein can be used to treat inflammation caused by: a physical cause such as burns, frostbite, physical injury (either blunt or penetrating), foreign bodies (including splinters, dirt, or debris), trauma, or ionizing radiation; a biological cause such as infection by a pathogen, an immune reaction due to hypersensitivity, or stress; or a chemical cause such as a chemical irritant, a toxin.

In some embodiments, the inflammation comprises acute inflammation. In some embodiments, the acute inflammation may be in response to one or more of the following: a wound (such as a cut, bruise, or burn); an infection (such as a bacterial, viral, fungal, or protist infection); exposure to a toxin or ionizing radiation; exposure to an allergen or antigen; and the presence of a foreign body (for example, a splinter) in a subject.

In some embodiments, the inflammation comprises chronic inflammation. In some embodiments, the chronic inflammation may be associated with a persistent form of acute inflammation, as described above, or may be associated with an inflammatory disorder.

The present methods may be used to treat or prevent inflammation in any part of the body, including but not limited to inflammation of: the central nervous system (such as encephalitis, myelitis, or meningitis); the peripheral nervous system (such as neuritis); the eye (such as dacryoadenitis, scleritis, episcleritis, or keratitis); the ear (such as otitis); the heart (such as endocarditis, myocarditis, or pericarditis); the vascular system (such as arteritis, phlebitis, or capillaritis); the respiratory system (such as sinusitis, rhinitis, pharyngitis, epiglottitis, laryngitis, tracheitis, bronchitis, pneumonitis, or pleurisy); the digestive system (such as stomatitis, gingivitis, glossitis, tonsillitis, sialadenitis, parotitis, cheilitis, pulpitis, gnathitis, oesophagitis, gastritis, gastroenteritis, enteritis, colitis, pancolitis, appendicitis, cryptitis, hepatitis, cholecystitis, or pancreatitis); the integumentary system (such as dermatitis or mastitis); the musculoskeletal system (such as arthritis, myositis, synovitis, tenosynovitis, or bursitis); the urinary system (such as nephritis, ureteritis, cystitis, or urethritis); the female reproductive system (such as oophoritis, salpingitis, endometritis, myometritis, parametritis, cervicitis, vaginitis, or vulvitis); the male reproductive system (such as orchitis, epididymitis, prostatitis, vasculitis, balanitis, or posthitis); the endocrine system (such as insulitis, hypophysitis, thyroiditis, parathyroiditis, or adrenalitis); or the lymphatic system (such a lymphangitis or lymphadenitis).

The present methods may also be used to treat or prevent inflammation resulting from an inflammatory disorder. In some embodiments, the methods described herein may be used as an analgesic to treat pain, for example a headache. In some embodiments, the methods described herein may be used to treat arthritis, including but not limited to rheumatoid arthritis, spondyloarthopathies, gouty arthritis, systemic lupus erythematosus, osteoarthritis, and juvenile arthritis. In some embodiments, the methods described herein may be used to treat asthma, bronchitis, menstrual cramps, tendinitis, bursitis, and skin related conditions such as psoriasis, eczema, burns and dermatitis. In some embodiments, the methods described herein may be used to treat gastrointestinal conditions such as inflammatory bowel disease, Crohn's disease, gastritis, irritable bowel syndrome, and ulcerative colitis. In some embodiments, the methods described herein may be used to treat inflammation present in a disorder including, but not limited to, vascular disease, migraine headaches, perarteritis nodosa, thyroiditis, aplastic anemia, Hodgkin's disease, scleroderma, rheumatic fever, type I diabetes, myasthenia gravis, sarcoidosis, nephrotic syndrome, Behcet's syndrome, polymyositis, hypersensitivity, conjunctivitis, gingivitis, swelling occurring after an injury, myocardial ischemia, and the like.

In some embodiments, the methods described herein may be used to treat or prevent inflammation associated with a disorder including, but not limited to, acne vulgaris, asthma, an autoimmune disease, an autoinflammatory disease, celiac disease, chronic prostatitis, colitis, diverticulitis, glomerulonephritis, hidradenitis suppurativa, hypersensitivities, inflammatory bowel disease, interstitial cystitis, lichen planus, mast cell activation syndrome, otitis, pelvic inflammatory disease, reperfusion injury, rheumatic fever, rheumatoid arthritis, rhinitis, sarcoidosis, transplant rejection, or vasculitis. In some embodiments, the methods described herein may be used to treat or prevent inflammation associated with atherosclerosis, cancer, or ischemic heart disease.

In some embodiments, the methods described herein may be used to treat a systemic inflammatory disorder or ameliorate or diminish one or more inflammatory symptoms of a system inflammatory disorder including, but not limited to, non-alcoholic fatty liver disease, non-alcoholic steatohepatitis, inflammatory bowel disease, Crohn's disease, ulcerative colitis, psoriasis, irritable bowel syndrome, ankylosing spondylitis, osteoporosis, rheumatoid arthritis, psoriatic arthritis, chronic obstructive pulmonary disease, atherosclerosis, pulmonary arterial hypertension, pyridoxine-dependent epilepsy, atopic dermatitis, rosacea, multiple sclerosis, systemic lupus erythematosus, lupus nephritis, sepsis, eosinophilic esophagitis, chronic kidney disease, fibrotic renal disease, chronic eosinophilic pneumonia, extrinsic allergic alveolitis, pre-eclampsia, endometriosis, polycystic ovary syndrome, or cyclophosphamide-induced hemorrhagic cystitis.

In some embodiments, the methods described herein may be used to treat inflammation resulting from a disorder selected from light chain deposition disease, IgA nephropathy, end-stage renal disease, gout, pseudogout, diabetic nephropathy, diabetic neuropathy, traumatic brain injury, noise-induced hearing loss, Alzheimer's disease, Parkinson's disease, Huntington disease, amyotrophic lateral sclerosis, primary biliary cirrhosis, primary sclerosing cholangitis, uterine leiomyoma, sarcoidosis, or chronic kidney disease.

In another aspect, a method for the treatment of pain in a subject in need thereof is provided comprising administering a composition comprising at least 1 wt. %, based upon the total weight of the composition, of a compound of formula (I), or a pharmaceutically acceptable salt or derivative thereof. The pain as treated by the methods described herein may include acute pain, chronic pain, nociceptive pain, neuropathic pain, cancer pain, or psychogenic pain.

Acute pain refers to mainly short pains that may last anywhere from a few seconds to at most 30 days, for example those resulting from the contact of skin with fire or subsequent to an insect sting. Chronic pain refers to pain that lasts for a duration of several months to several years or more; chronic pain typically accompanies other inflammatory or neuropathic pathologies.

Nociceptive pain refers to pain caused by stimulation of sensory nerve fibers (nociceptors) that response to stimuli approaching or exceeding harmful intensity and may be classified according to the mode of noxious stimulation, such as thermal (e.g., heat or cold), mechanical (e.g., crushing, tearing, shearing, etc.), or chemical (e.g., acid in a cut or chemicals released during inflammation). Nociceptive pain may also be classified according to the site of origin. Visceral pain originates from visceral structures (e.g., heart, liver, or intestines) which are highly sensitive to stretch, ischemia, or inflammation but are otherwise insensitive to other stimuli. Visceral pain is diffuse, difficult to locate, and often refers to a distant, usually superficial, structure and may be accompanied by nausea and vomiting. Deep somatic pain is initiated by stimulation of nociceptors in ligaments, tendons, bones, blood vessels, fasciae and muscles and is dull, aching, and poorly-localized pain. Superficial pain, such as pain resulting from minor wounds and burns, is initiated by activation of nociceptors in the skin or other superficial tissue and is sharp, well-defined and clearly located.

Neuropathic pain is caused by damage or disease affecting any part of somatosensory system. Neuropathic pain may be peripheral, central, or mixed neuropathic pain. Peripheral neuropathic pain is typically described as burning, tingling, electrical, stabbing, or feeling like pins and needles.

Cancer pains are those that develop in the context of cancer as a disease either as nociceptive pain related to cancer development or neuropathic pain due to lesional invasion or as the result of treatment.

Psychogenic pain is pain caused, increased, or prolonged by mental, emotional, or behavioral factors, and often accompanies mental pathologies such as depression or schizophrenia.

In some embodiments, the composition may comprise the compound of formula (I) in an amount of at least 1 wt. %, at least 5 wt. %, at least 10 wt. %, at least 20 wt. %, at least 30 wt. %, at least 40 wt. %, at least 50 wt. %, at least 60 wt. %, at least 70 wt. %, or more based upon the total weight of the composition. In some embodiments, the composition may comprise the compound of Formula (I) in an amount from 1 to 70 wt. %, from 5 to 70 wt. %, from 10 to 70 wt. %, from 20 to 70 wt. %, from 30 to 70 wt. %, from 40 to 70 wt. %, from 50 to 70 wt. %, from 60 to 70 wt. %, from 1 to 60 wt. %, from 5 to 60 wt. %, from 10 to 60 wt. %, from 20 to 60 wt. %, from 30 to 60 wt. %, from 40 to 60 wt. %, from 50 to 60 wt. %, from 1 to 50 wt. %, from 5 to 50 wt. %, from 10 to 50 wt. %, from 20 to 50 wt. %, from 30 to 50 wt. %, from 40 to 50 wt. %, from 1 to 40 wt. %, from 5 to 40 wt. %, from 10 to 40 wt. %, from 20 to 40 wt. %, from 30 to 40 wt. %, from 1 to 30 wt. %, from 5 to 30 wt. %, from 10 to 30 wt. %, from 20 to 30 wt. %, from 1 to 20 wt. %, from 5 to 20 wt. %, from 10 to 20 wt. %, from 1 to 10 wt. %, from 5 to 10 wt. %, or 1 to 5 wt. %, based upon the total weight of the composition.

Combination Therapy

In some embodiments, the compositions as used in the methods described herein can further comprise or be administered in combination with other therapies. The composition described herein can be administered simultaneously, sequentially, or at distinct time points as part of the same therapeutic regimen.

In some embodiments, the composition as used in the methods described herein can further comprise or be administered in combination with acetaminophen (paracetamol).

In some embodiments, the composition as used in the methods described herein can further comprise or be administered in combination with a non-steroidal anti-inflammatory drug, including but not limited to: aspirin, diflunisal, salicylic acid and its salts, salsalate, ibuprofen, fenoprofen, flurbiprofen, dexibuprofen, ketoprofen, oxaprozin, naproxen, dexketoprofen, loxoprofen, indomethacin, etodolac, aceclofenac, tolmetin, ketorolac, nabumetone, sulindac, diclofenac, piroxicam, tenoxicam, lornoxicam, phenylbutazone, meloxicam, droxicam, isoxicam, mefenamic acid, meclofenamic acid, flufenamic acid, tolfenamic acid, celecoxib, valdecoxib, lumiracoxib, firocoxib, rofecoxib, parecoxib, etoricoxib, nimesulide, clonixin, licofelone, and harpagide.

In some embodiments, the composition as used in the methods described herein can further comprise or be administered in combination with an opioid, including but not limited to: opium alkaloids and derivatives such as codeine, thebaine, morphine, oripavine, diacetylmorphine, diacetyldihydromorphine, methyldesorphine, nicomorphine, acetylpropionylmorphine, dibenzoylmorphine, dipropanoylmorphine, desomorphine, dihydrocodeine, ethylmorphine, heterocodeine, buprenorphine, hydrocodone, oxycodone, etorphine, hydromorphone, oxymorphone, fentanyl, sufentanil, ohmefentanyl, alphamethylfentanyl, remifentanil, alfentanil, carfentanyl, pethidine, allylprodine, promedol ketobemidone, prodine, desmethylprodine, phenethylphenylacetoxypiperidine, propoxyphene, methadone, loperamide, dextropropoxyphene, dipianone, dextromoramide, levomethadyl acetate, bezitramide, difenoxin, piritramide, diphenoxylate, dezocine, pentazocine, phenazocine, buprenorphine, dihydroetorphine, etorphine, butorphanol, levorphanol, racemethorphan, nalbuphine, levomethorphan, lefetamine, tilidine, buccinazine, menthol, tramadol, 7-hydroxymitragynine, meptazinol, tapentadol, mitragynine, or eluxadoline; or opioid antagonists such as nalmefene, methylnaltrexone, naloxegol, naloxone, or naltrexone.

In some embodiments, the composition as used in the methods described herein can further comprise or be administered in combination with an antidepressant, including but not limited to: duloxetine, venlafaxine, milnacipran, amitriptyline, nortriptypine, desipramine, or bupropion.

In some embodiments, the composition as used in the methods described herein can further comprise or be administered in combination with an anticonvulsant, including but not limited to: pregabalin, gabapentin, carbamazepine, or oxcarbazepine.

In some embodiments, the composition as used in the methods described herein can further comprise or be administered in combination with a topical anesthetic, including but not limited to: benzocaine, butamben, dibucaine, lidocaine, oxybuprocaine, pramoxine, proparacaine, proxymetacaine, and tetracaine. In some embodiments, the composition as used in the methods described herein can further comprise or be administered in combination with capsaicin.

In some embodiments, the composition as used in the methods described herein can further comprise or be administered in combination with caffeine.

In some embodiments, the composition as used in the methods described herein can further comprise or be administered in combination with an N-methyl-D-aspartate receptor antagonist including, but not limited to: memantine, ketamine, or dextromethorphan.

Methods of Administration

The compounds as used in the methods described herein can be administered by any suitable method and technique presently or prospectively known to those skilled in the art. For example, the active components described herein can be formulated in a physiologically- or pharmaceutically-acceptable form and administered by any suitable route known in the art including, for example, oral and parenteral routes of administering. As used herein, the term "parenteral" includes subcutaneous, intradermal, intravenous, intramuscular, intraperitoneal, and intrasternal administration, such as by injection. Administration of the active components of their compositions can be a single administration, or at continuous and distinct intervals as can be readily determined by a person skilled in the art.

Compositions, as described herein, comprising an active compound and an excipient of some sort may be useful in a variety of medical and non-medical applications. For example, pharmaceutical compositions comprising an active compound and an excipient may be useful for the treatment or prevention of inflammation in a subject in need thereof.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Exemplary excipients include, but are not limited to, any non-toxic, inert solid, semisolid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray. In some embodiments, the active compounds disclosed herein are administered topically.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid. Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacrylic acid/acrylamide copolymer, polyalkylene oxides such as polyethylene oxide, polypropylene oxide, poly(ethylene oxide-propylene oxide), and a Pluronic polymer, polyoxy ethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly (meth) acrylic acid, and esters amide and hydroxy alkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Methods of Isolating Compounds of Formula (I)

Further provided herein are methods of isolating a compound of Formula (I) from pine rosin, the method comprising:

(a) contacting pine rosin with a solvent such that a portion of the compound of formula (I) is extracted into the solvent to provide a first extract;

(b) removing the solvent to provide a first concentrate;

(c) subjecting the first concentrate to a separation technique that provides a plurality of fractions;

(d) testing each fraction within the plurality fractions for inhibitory activity against COX-2 or TNF-α;

(e) removing the solvent from the fraction within the plurality of fractions with the highest inhibitory activity against COX-2 or TNF-α to provide a second concentrate; and

(f) repeating steps (c) to (e) until the concentrate contains the compound of formula (I) in a purity of greater than 90%.

The separation technique may comprise any such technique as would be known to those having skill in the art, such as various types of chromatography including silica gel column chromatography or high-performance liquid chromatography.

The fractions isolated may be tested for activity against COX-2 or TNF-α using assays as would be known to those having skill in the art. Representative examples of such assays that could be used include a COX-2 inhibitory fluorometric assay or a TNF-α inhibitory fluorometric assay, each of which are commercially available from numerous suppliers.

In another aspect, the present disclosure further provides the following embodiments:

Embodiment 1. A method for treating inflammation in a subject in need thereof comprising administering a composition comprising at least 1 wt. % based on the total weight of the composition of a compound of formula (I):

or a pharmaceutically acceptable salt thereof.

Embodiment 2. A method for diminishing or ameliorating one or more symptoms caused by inflammation in a subject in need thereof comprising administering a composition comprising at least 1 wt. % based on the total weight of the composition of a compound of formula (I):

or a pharmaceutically acceptable salt thereof.

Embodiment 3. A method for preventing inflammation in a subject in need thereof comprising administering a composition comprising at least 1 wt. % based on the total weight of the composition of a compound of formula (I):

or a pharmaceutically acceptable salt thereof.

Embodiment 4. The method of any one of embodiments 1-3, wherein the inflammation is acute inflammation.

Embodiment 5. The method of any one of embodiments 1-3, wherein the inflammation is chronic inflammation.

Embodiment 6. The method of any one of embodiments 1-3, wherein the inflammation is associated with an inflammatory disorder.

Embodiment 7. The method of any one of embodiments 1-3, wherein the inflammation is selected from encephalitis, myelitis, meningitis, neuritis, dacryoadenitis, scleritis, episcleritis, keratitis, otitis, endocarditis, myocarditis, pericarditis, arteritis, phlebitis, capillaritis, sinusitis, rhinitis, pharyngitis, epiglottitis, laryngitis, tracheitis, bronchitis, pneumonitis, pleurisy, stomatitis, gingivitis, glossitis, tonsillitis, sialadenitis, parotitis, cheilitis, pulpitis, gnathitis, oesophagitis, gastritis, gastroenteritis, enteritis, colitis, pancolitis, appendicitis, cryptitis, hepatitis, cholecystitis, pancreatitis, dermatitis, mastitis, arthritis, myositis, synovitis, tenosynovitis, bursitis, nephritis, ureteritis, cystitis, urethritis, oophoritis, salpingitis, endometritis, myometritis, parametritis, cervicitis, vaginitis, vulvitis, orchitis, epididymitis, prostatitis, vasculitis, balanitis, posthitis, insulitis, hypophysitis, thyroiditis, parathyroiditis, adrenalitis, lymphangitis and lymphadenitis.

Embodiment 8. The method of any one of embodiments 1-3, wherein the inflammation is associated with arthritis.

Embodiment 9. The method of embodiment 8, wherein the arthritis is selected from rheumatoid arthritis, spondyloarthopathies, gouty arthritis, systemic lupus erythematosus, osteoarthritis, and juvenile arthritis.

Embodiment 10. The method of any one of embodiments 1-3, wherein the inflammation is associated with asthma, bronchitis, menstrual cramps, tendinitis, bursitis, psoriasis, eczema, burns or dermatitis.

Embodiment 11. The method of any one of embodiments 1-3, wherein the inflammation is associated with a gastrointestinal condition.

Embodiment 12. The method of embodiment 11, wherein the gastrointestinal condition is selected from inflammatory bowel disease, Crohn's disease, gastritis, irritable bowel syndrome, and ulcerative colitis.

Embodiment 13. The method of any one of embodiments 1-3, wherein the inflammation is associated with vascular disease, migraine headaches, perarteritis nodosa, thyroiditis, aplastic anemia, Hodgkin's disease, scleroderma, rheumatic fever, type I diabetes, myasthenia gravis, sarcoidosis, nephrotic syndrome, Behcet's syndrome, polymyositis, hypersensitivity, conjunctivitis, gingivitis, swelling occurring after an injury, or myocardial ischemia.

Embodiment 14. A method for the treatment of a systemic inflammatory disorder in a subject in need thereof comprising administering a composition comprising at least 1 wt. % based on the total weight of the composition of a compound of formula (I):

(I)

or a pharmaceutically acceptable salt thereof.

Embodiment 15. A method for ameliorating or diminishing one or more inflammatory symptoms of a systemic inflammatory disorder in a subject in need thereof comprising administering a composition comprising at least 1 wt. % based on the total weight of the composition of a compound of formula (I):

(I)

or a pharmaceutically acceptable salt thereof.

Embodiment 16. The method of any one of embodiments 14 or 15, wherein the systemic inflammatory disorder is selected from non-alcoholic fatty liver disease, non-alcoholic steatohepatitis, inflammatory bowel disease, Crohn's disease, ulcerative colitis, psoriasis, irritable bowel syndrome, ankylosing spondylitis, osteoporosis, rheumatoid arthritis, psoriatic arthritis, chronic obstructive pulmonary disease, atherosclerosis, pulmonary arterial hypertension, pyridoxine-dependent epilepsy, atopic dermatitis, rosacea, multiple sclerosis, systemic lupus erythematosus, lupus nephritis, sepsis, eosinophilic esophagitis, chronic kidney disease, fibrotic renal disease, chronic eosinophilic pneumonia, extrinsic allergic alveolitis, pre-eclampsia, endometriosis, polycystic ovary syndrome, and cyclophosphamide-induced hemorrhagic cystitis.

Embodiment 17. A method for the treatment of pain in a subject in need thereof comprising administering a composition comprising at least 1 wt. % based on the total weight of the composition of a compound of formula (I):

(I)

or a pharmaceutically acceptable salt thereof.

Embodiment 18. The method of embodiment 17, wherein the pain includes acute pain.

Embodiment 19. The method of embodiment 17, wherein the pain includes chronic pain.

Embodiment 20. The method of embodiment 17, wherein the pain includes nociceptive pain.

Embodiment 21. The method of embodiment 17, wherein the pain includes neuropathic pain.

Embodiment 22. The method of embodiment 17, wherein the pain includes cancer pain.

Embodiment 23. The method of embodiment 17, wherein the pain includes psychogenic pain.

Embodiment 24. The method of any one of embodiment 1-23, wherein the composition further comprises an additional therapeutic.

Embodiment 25. The method of embodiment 24, wherein the additional therapeutic is acetaminophen.

Embodiment 26. The method of embodiment 24, wherein the additional therapeutic is a non-steroidal anti-inflammatory drug.

Embodiment 27. The method of embodiment 24, wherein the additional therapeutic is an opioid.
Embodiment 28. The method of embodiment 24, wherein the additional therapeutic is an antidepressant.
Embodiment 29. The method of embodiment 24, wherein the additional therapeutic is an anticonvulsant.
Embodiment 30. The method of embodiment 24, wherein the additional therapeutic is a topical anesthetic.
Embodiment 31. The method of embodiment 24, wherein the additional therapeutic is capsaicin.
Embodiment 32. The method of embodiment 24, wherein the additional therapeutic is caffeine.
Embodiment 33. The method of embodiment 24, wherein the additional therapeutic is an N-methyl-D-aspartate receptor antagonist.
Embodiment 34. The method of any one of embodiments 1-33, wherein the compound of formula (I) is present in the composition in an amount of at least 5 wt. %, at least 10 wt. %, at least 20 wt. %, at least 30 wt. %, or more based upon the total weight of the composition.
Embodiment 35. The method of any one of embodiments 1-34, wherein the subject is a human.
Embodiment 36. A method of isolating from pine rosin a compound of formula (I)

(I)

the method comprising:
(a) contacting the pine rosin with a solvent such that a portion of the compound of formula (I) is extracted into the solvent to provide a first extract;
(b) removing the solvent to provide a first concentrate;
(c) subjecting the first concentrate to a separation technique that provides a plurality of fractions;
(d) testing each fraction within the plurality fractions for inhibitory activity against COX-2 or TNF-α;
(e) removing the solvent from the fraction within the plurality of fractions with the highest inhibitory activity against COX-2 or TNF-α to provide a second concentrate; and
(f) repeating steps (c) to (e) until the concentrate contains the compound of formula (I) in a purity of greater than 90%.

A number of embodiments of the disclosure have been described. Nevertheless, it will be understood that various modifications may be made without departing from the spirit and scope of the invention. Accordingly, other embodiments are within the scope of the following claims.

EXAMPLES

By way of non-limiting illustration, examples of certain embodiments of the present disclosure are given below.
Isolation of Compound of Formula (I)
The crude sample provided was dissolved in Ethyl acetate and dried down on Silica gel in a 1:3 ratio. Medium pressure chromatography was performed using a Teledyne-Isco combi-flash Torrent system. A 750 gram silica column was used with a Hexanes to Ethyl acetate gradient, which gave 11 fractions. Fraction A was then subjected to high pressure liquid chromatography on a preparative Silica NP column (250×20 mm), with a gradient between Hexanes to 20% ethyl acetate, which gave 4 fractions. The active fraction was further purified, with a gradient of Hexanes to 100% ethyl acetate on a preparative Silica NP column (250×20 mm), which gave 23 fractions. Fraction 17 was subjected to two rounds of NP hplc using an analytical Silica column (250×10 mm), which gave the final pure compound. An LC-20AD Shimadzu system and an SPD-20A UV detector was used for the hplc separations. All steps were guided using bioassay data from the COX-2 and TNF-α assays. The fractions for each separation step were subjected to both assays and the active ones were further purified. Fraction A was selected due to its higher activity compared to the rest.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:
1. A method for inhibiting the activity of TNF-α in a subject in need thereof, wherein diseases treatable by such inhibition include inflammation and pain, the method comprising administering a composition comprising at least 1 wt. % based on the total weight of the composition of a compound of formula (I):

(I)

or a pharmaceutically acceptable salt thereof.

2. The method of claim 1, wherein the inflammation is acute inflammation.

3. The method of claim 1, wherein the inflammation is chronic inflammation.

4. The method of claim 1, wherein the inflammation is associated with an inflammatory disorder.

5. The method of claim 1, wherein the inflammation is selected from encephalitis, myelitis, meningitis, neuritis, dacryoadenitis, scleritis, episcleritis, keratitis, otitis, endocarditis, myocarditis, pericarditis, arteritis, phlebitis, capillaritis, sinusitis, rhinitis, pharyngitis, epiglottitis, laryngitis, tracheitis, bronchitis, pneumonitis, pleurisy, stomatitis, gingivitis, glossitis, tonsillitis, sialadenitis, parotitis, cheilitis, pulpitis, gnathitis, oesophagitis, gastritis, gastroenteritis, enteritis, colitis, pancolitis, appendicitis, cryptitis, hepatitis, cholecystitis, pancreatitis, dermatitis, mastitis, arthritis, myositis, synovitis, tenosynovitis, bursitis, nephritis, ureteritis, cystitis, urethritis, oophoritis, salpingitis, endometritis, myometritis, parametritis, cervicitis, vaginitis, vulvitis, orchitis, epididymitis, prostatitis, vasculitis, balanitis, posthitis, insulitis, hypophysitis, thyroiditis, parathyroiditis, adrenalitis, lymphangitis and lymphadenitis.

6. The method of claim 1, wherein the inflammation is associated with arthritis.

7. The method of claim 6, wherein the arthritis is selected from rheumatoid arthritis, spondyloarthopathies, gouty arthritis, systemic lupus erythematosus, osteoarthritis, and juvenile arthritis.

8. The method of claim 1, wherein the inflammation is associated with asthma, bronchitis, menstrual cramps, tendinitis, bursitis, psoriasis, eczema, burns or dermatitis.

9. The method of claim 1, wherein the inflammation is associated with a gastrointestinal condition.

10. The method of claim 9, wherein the gastrointestinal condition is selected from inflammatory bowel disease, Crohn's disease, gastritis, irritable bowel syndrome, and ulcerative colitis.

11. The method of claim 1, wherein the inflammation is associated with vascular disease, migraine headaches, perarteritis nodosa, thyroiditis, aplastic anemia, Hodgkin's disease, scleroderma, rheumatic fever, type I diabetes, myasthenia gravis, sarcoidosis, nephrotic syndrome, Behcet's syndrome, polymyositis, hypersensitivity, conjunctivitis, gingivitis, swelling occurring after an injury, or myocardial ischemia.

12. The method of claim 1, wherein the composition further comprises an additional therapeutic.

13. The method of claim 1, wherein the compound of formula (I) is present in the composition in an amount of at least 5 wt. %, at least 10 wt. %, at least 20 wt. %, at least 30 wt. %, or more based upon the total weight of the composition.

14. The method of claim 1, wherein the subject is a human.

15. The method of claim 1, wherein the pain is selected from acute pain, chronic pain, nociceptive pain, neuropathic pain, cancer pain, and psychogenic pain.

* * * * *